(12) United States Patent
Imura et al.

(10) Patent No.: US 6,649,198 B2
(45) Date of Patent: Nov. 18, 2003

(54) PROCESS FOR PRODUCING BREAD

(75) Inventors: Toshiaki Imura, Ibaraki (JP); Takashi Onaka, Ibaraki (JP); Hideo Muromachi, Tokyo (JP); Hideki Kawasaki, Ibaraki (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/851,146

(22) Filed: May 9, 2001

(65) Prior Publication Data

US 2001/0055634 A1 Dec. 27, 2001

(30) Foreign Application Priority Data

May 12, 2000 (JP) .......................... 2000-141034

(51) Int. Cl.[7] .................................. A21D 8/02
(52) U.S. Cl. ........................................ 426/19; 426/551
(58) Field of Search ............................ 426/19, 653, 62, 426/549, 25, 551, 561; 435/255.2

(56) References Cited

U.S. PATENT DOCUMENTS 4,895,802 A    1/1990   Sone et al. ................ 426/11

FOREIGN PATENT DOCUMENTS

| JP | 4-91782   | 3/1992 |
| JP | 6-133703  | 5/1994 |
| JP | 6-197749  | 7/1994 |
| JP | 2810703   | 7/1998 |
| JP | 2886561   | 2/1999 |

*Primary Examiner*—Keith Hendricks
(74) *Attorney, Agent, or Firm*—Fitzpatrick, Cella, Harper & Scinto

(57) ABSTRACT

The present invention provides an yeast capable of making bread excellent in flavor and taste and weak in fermentation smell, a dough containing the yeast, a process for making bread using the yeast or the dough and the bread made by the method. The present invention relates to the yeast which belongs to the genus Saccharomyces and generates 35 ppm or less of isoamyl alcohol, a ratio of 2 or less of isoamyl alcohol to isobutyl alcohol, 1.5 ppm or more of diacetyl in the bread and 2 ml or more of carbon dioxide gas per 1 g of the dough, a screening method for selecting the yeast, a process for making bread containing the yeast and the dough and bread made by the method.

5 Claims, No Drawings

PROCESS FOR PRODUCING BREAD

TECHNICAL FIELD

The present invention relates to an yeast, a dough, a process for making bread and a bread made by the process.

BACKGROUND OF THE INVENTION

It is considered that, in foods and beverages such as alcoholic drinks and fermented seasonings, components of flavor, fragrance or aroma (hereinafter referred to as "flavor" collectively) which are contained in esters, alcohols or the like as produced by yeast to be used are determinative of characteristics of flavor of those foods and beverages to give a great influence on qualities thereof.

In a bread-making industry, it has been in demand to make bread having a good flavor and taste in line with an increasing inclination toward gourmet in recent years.

For obtaining bread having a good flavor, there have been known methods of increasing an amount of isoamyl alcohol or isobutyl alcohol to be produced by yeast (Japanese Patent Nos. 2,810,703 and No. 2,886,561 and Japanese Published Unexamined Patent Application Nos. 91782/1992 and 133703/1994).

However, it has been known that bread having rich contents of higher alcohols, for example, isoamyl alcohol and isobutyl alcohol is liable to mask a favorable flavor and taste inherent in ingredients of bread. Further, it has not been known how ratio between isoamyl alcohol and isobutyl alcohol gives an effect to the flavor and taste of bread. It has been known that diacetyl is a substance which has an unpleasant smell called as "stuffy (sour) smell" or "DA smell" and gives a bad effect to qualities of alcoholic drinks (U.S. Pat. No. 4,895,802 and Japanese Published Unexamined Patent Application No. 197749/1994). However, a relation between an amount of diacetyl to be produced by yeast and the flavor and taste of bread has not been known.

For production of buns, sugar-resistant yeast has been used (Basic Knowledge for New Bread Making, Pan News Co., Ltd. p. 30, (1981)); however, a relation of the sugar-resistant yeast and the taste of bread has not been known.

SUMMARY OF THE INVENTION

An object of the present invention is to provide a yeast capable of making bread excellent in flavor and taste and weak in fermentation smell, a dough containing the yeast, a process for making bread using the yeast or the dough and the bread made by the method.

The present invention relates to yeast which belongs to the genus Saccharomyces and has characteristics (1) and (2) to be described below, dough containing the yeast, a process for making bread using the yeast or the dough and bread made by the method. Further, the present invention relates to a screening method for selecting yeast which belongs to the genus Saccharomyces, has the characteristics (1) and (2) to be described below and is used for making bread excellent in flavor and taste and/or weak in fermentation smell, the yeast obtainable by the method, a dough containing the yeast, a process for making bread using the yeast or the dough and a bread obtainable by the method.

Characteristic (1) is that the concentration of isoamyl alcohol is 35 ppm or below, preferably 10 to 35 ppm, the concentration of diacetyl is 1.5 ppm or above, preferably 1.5 to 3.0 ppm, and the ratio of isoamyl alcohol to isobutyl alcohol in concentration is 2 or below, preferably 1 to 2 ppm; said isoamyl alcohol, isobutyl alcohol and diacetyl being contained in a headspace gas, derived from bread which bread is made by the steps of (1) to (8):

(1) mixing 1050 g of strong flour, 30 g of a compressed product of said yeast, 1.5 g of yeast food, for example, Pandia C-500, Pandia C-100, Pandia C-200 and Pandia C-300 (all available from Kyowa Hakko Kogyo Co., Ltd.) and 630 g of water by a bread mixer at a low speed for 3 minutes and, then, at a low/medium speed for 2 minutes such that a temperature of the resultant mixture becomes 24° C. to prepare dough;

(2) fermenting the resultant dough prepared by the step (1) at 28° C. for 4 hours to prepare fermented dough;

(3) adding 450 g of strong flour, 75 g of sugar, 30 g of salt, 30 g of skim milk and 390 g of water to the thus fermented dough prepared by the step (2); mixing the resultant mixture at a low speed for 3 minutes and, then, a low/medium speed for 2 minutes by a bread mixer for example, SS type 151, SS type 111 (both available from Kanto Kongoki Industrial Co., Ltd.), Mighty 30 type (available from Aicohsha Mfg. Co., Ltd., etc.); adding 75 g of shortening to the thus mixed mixture; further, mixing the resultant mixture at a low speed for 2 minutes, a low/medium speed for 3 minutes, and then, a medium/high speed for 3 minutes by a bread mixer such that a temperature of the resultant mixture becomes 27° C. to prepare dough;

(4) allowing the dough prepared by the step (3) to stand intact at a temperature of between 20° C. and 25° C. for 20 minutes;

(5) dividing the thus stood intact dough prepared by the step (4) to obtain 6 pieces of dough each having 210 g; molding the thus obtained 6 pieces of dough in ball form;

(6) allowing the 6 pieces of dough prepared by the step (5) to stand intact at a temperature of between 20° C. and 25° C. for 20 minutes;

(7) punching the thus stood intact 6 pieces of dough obtained by the step (6); placing the thus punched 6 pieces of dough in a 3-pound bread mold; molding the thus placed dough appropriately; fermenting the thus molded dough to allow it to rise to 80% of the inner volume of the mold at 38° C. and in 85% humidity; and (8) baking the thus fermented dough prepared by the step (7) in an oven at 210° C. for 35 minutes, said headspace gas being generated from said bread according to the steps of (a) to (c):

(a) adding liquid nitrogen to 8 g of a central portion of said bread; grinding the portion by a mortar into powders;

(b) introducing 3 g of the resultant powders prepared by the step (a) into a 22 ml sample bottle; sealing the bottle;

(c) holding the sealed bottle prepared by the step (b) at 60° C. for 15 minutes; and said concentrations of isoamyl alcohol, isobutyl alcohol and diaceyl being determined by quantitatively analyzing said headspace gas in the sealed bottle obtained by the step (c) by means of gas chromatography.

The characteristics (2) is that an amount of carbon dioxide gas is 2 ml or above/g, preferably 2 to 5 ml/g, of dough prepared by step (i) below, when measured by quantitatively analyzing carbon dioxide gas generated at 30° C. for 2 hours by means of a fermograph;

said carbon dioxide being generated according to the steps (i) to (iii):

(i) mixing a yeast suspension comprising 100 g of strong flour, 3 g of a compressed product of said yeast and 20 g of water, and an aqueous solution comprising 30 g of sugar, 0.5 g of salt and 32 ml of water by a complete mixer at 100 rpm for 2 minutes;

(ii) introducing 20 g of the resultant dough prepared by the step (i) into a 225 ml sample bottle; sealing the bottle, and (iii) holding the thus sealed bottle prepared by the step (ii) at 30° C. for 5 minutes.

DETAILED DESCRIPTION OF THE INVENTION

A compressed product of yeast described in characteristics of the present invention can be produced by a method described below.

10 g of glucose, 5 g of peptone, 3 g of yeast extract, 3 g of malt extract, 20 g of agar are added to 1 liter of water. The solution is controlled at pH 6 and, then, is sterilized at 120° C. for 20 min. to prepare a YM medium which is then used for preparing a slant. On this slant, a platinum loopful of yeast of the present invention is inoculated, and the yeast-inoculated slant is incubated at 30° C. for 2 days to prepare an active slant. The thus obtained active slant is added to 5 ml of sterilized water to allow cells to be suspended therein. 2.5 ml of the resultant suspension is inoculated on a molasses medium (comprising 300 ml of water, molasses having a sugar content of 3%, 0.33 g of potassium phosphate and 0.135 g of urea) in a 2-liter Erlenmeyer flask with inclined baffles which has been sterilized at 120° C. for 20 minutes and, then, incubated under shaking (220 rpm) at 30° C. for 24 hours. All of the above-incubated liquid medium is added to a medium (comprising 1.8 liters of water, 43.2 g of ammonium sulfate, 14 g of potassium phosphate and 2.2 g of magnesium sulfate) in a 5-liter jar fermentor which has been sterilized at 120° C. for 20 minutes and, then, subjected to a feeding culture at 30° C. for 30 hours using 800 ml of molasses medium (total sugar content of 48%) which has been sterilized at 120° C. for 5 minutes while the pH thereof is being controlled at 5.0 with ammonia water during the feeding culture.

After the feeding culture is completed, the culture is centrifuged to collect cells. The thus collected cells are rinsed and dehydrated to obtain a compressed product of yeast. The term "compressed product of yeast" described in the characteristics of the present invention denotes a product that a ratio of the weight of yeast in a dry state (dried yeast) in the above-described compressed product corresponds to 33 wt %.

Such a ratio of the weight of yeast in a dry state in the compressed product can be determined by a method described below.

About 3 g (A) of the compressed product of yeast is weighed and dried at 105° C. for 5 hours. A weight (B) of the thus dried product is weighed. Then, the ratio (%) of the weight of the dried product is calculated by the following formula:

The ratio of the weight of the dried product (%)=100×(B/A).

When characteristics of the present invention are evaluated, the compressed product in which the ratio of the weight of yeast in a dry state is controlled to be between 30 wt % and 35 wt % is used. In order to obtain the same result from the compressed product of yeast practically used and another compressed product of yeast in which the ratio of the weight of yeast in a dry state corresponds to 33 wt %, an amount of the compressed product of yeast to be practically used is compensated by the following formula and the thus compensated amount is used for evaluation of the characteristics of the present invention:

An amount of usage (g) of the compressed product of yeast=(a)×33/(b)

wherein (a) represents an amount of the compressed product of yeast described in the characteristics of the present invention; and (b) represents the ratio of the weight of the compressed product in a dry state.

Values of concentrations of isoamyl alcohol, isobutyl alcohol and diacetyl described in the present invention can be obtained by quantitatively analyzing a gas contained in the headspace (headspace gas) of a sample bottle by gas chromatography under measuring conditions described below.

Apparatus:

Head space auto sampler 7000 (available from Tekmar Company, U.S.A.); HP589011 (available from Hewlett-Packard Company, U.S.A.)

Column:

Capillary column TC-WAX 60 m (length)×0.25 μm (film thickness)×0.25 mm (inner diameter) (available from GL Sciences Inc.)

Measuring conditions:

Column temperature: Initial temperature, 40° C.; initial holding time, 10 minutes; temperature increasing rate, 4° C./min.; final temperature, 240° C.; final holding time, 10 min.

Carrier gas: helium (flow rate, 1 ml/min.)

Injection temperature: 150° C.

Ion source temperature: 280° C.

Uptaking mass range: m/z, 35–200

Quantitative analyses of isoamyl alcohol, isobutyl alcohol and diacetyl are performed by using an internal standard method in which cyclohexanol is employed as an internal standard. Standard calibration curves of isoamyl alcohol, isobutyl alcohol and diacetyl are constructed by a method described below. 8 g of a central portion of commercially available bread is treated with liquid nitrogen and ground into powders in a mortar. 3 g of the powders are placed in a 22 ml sample bottle. Various concentrations (parts by weight) of isoamyl alcohol, isobutyl alcohol and diacetyl relative to the weight of the powders are added to respective sample bottles which are then sealed hermetically. The hermetically sealed sample bottle is held at 60° C. for 15 minutes to generate a headspace gas. The generated headspace gas is analyzed by gas chromatography. The standard calibration curves are constructed by concentrations of isoamyl alcohol, isobutyl alcohol and diacetyl which have been added and increments of peak areas generated thereby. Concentrations of isoamyl alcohol, isobutyl alcohol and diacetyl in bread can be determined by making use of thus obtained respective standard calibration curves.

According to the screening method of the present invention, can be separated (screens out) yeast belonging to the genus Saccharomyces having the above-described characteristics, preferably, *Saccharomyces cerevisiae* from a fermented product obtained by adding water to, for example, natural products, such as flour, cereal (e.g., rye) flour and the like. Further, a strain having the above-described characteristics can be obtained by a selecting operation after performing mutagenesis on a commercially available yeast belonging to the genus Saccharomyces, such as bread yeast, sake yeast, wine yeast, beer yeast, miso/soy sauce yeast by means of a known mutation-inducing method such as irradiation with ultraviolet light and radiation, a treatment by a mutation-inducing agent such as ethylmethane sulfonate and N-methyl-N'-nitro-N-nitrosoguanidine, gene engineering and the like.

Specific exemplary yeast of the present invention include *Saccharomyces cerevisiae* H-9444 (hereinafter referred to as "H-9444 strain"), *Saccharomyces cerevisiae* YHK2057 (hereinafter referred to as "YHK2057 strain") and *Saccharomyces cerevisiae* YHK2058 (hereinafter referred to as "YHK2058 strain").

The H-9444 strain is a strain selected from a flour fermentation product and was deposited as FERM BP-7153 with The National Institute of Bioscience and Human-Technology, Agency of Industrial Science and Technology located at 1–3, Higashi 1-chome, Tsukuba-shi, Ibaraki-ken, 305–8566 Japan on May 10, 2000 under the Budapest Treaty.

The YHK2057 is a mutant strain obtained by a method described below.

One platinum loopful of Dia Yeast (commercially available from Kyowa Hakko Kogyo Co., Ltd.) was inoculated on 50 ml of YPD medium (comprising 1% yeast extract, 2% polypeptone and 2% glucose) and cultured at 30° C. for 16 hours by shaking. After culturing was completed, the cells were collected by centrifugation. The collected cells were washed twice with sterilized water and then suspended in 27.6 ml of 0.2M phosphoric acid buffer. To the resultant suspension was added 1.5 ml of 40% glucose solution and 0.9 ml of ethylmethane sulfonate and mildly shaken at 30° C. for 180 minutes. The thus treated cells were collected, neutralized by 5% sodium thiosulfate solution, washed three times with sterilized water and suspended in 10 ml of sterilized water. The resultant suspension was spread on YPD plate medium and cultured at 30° C. for 48 hours to grow colonies. From such colonies, YHK2057 strain was obtained as a strain which increased an amount of diacetyl and lowered a ratio of isoamyl alcohol/isobutyl alcohol in a baked bread compared with those generated by a parent strain thereof.

The YHK2058 strain is a mutant strain obtained by the same mutagenizing treatment as in YHK2057 except that Dia Yeast was replaced by Dia Yeast FT-S (available from Kyowa Hakko Kogyo Co., Ltd.) as a parent strain.

Yeast of the present invention can be cultured under an ordinary culture condition, namely, in a medium containing carbon sources, nitrogen sources, inorganic substances, amino acids, vitamins and the like under an aerobic condition at a temperature of between 27° C. and 32° C.

As the carbon sources, glucose, sucrose, a starch hydrolyzate, molasses, etc. can be used and, preferably, blackstrap molasses is used.

As the nitrogen sources, ammonia, ammonium chloride, ammonium sulfate, ammonium carbonate, ammonium acetate, urea, yeast extract, corn steep liquor, etc. can be used.

As the inorganic substances, magnesium phosphate, potassium phosphate, etc. can be used; as the amino acids, glutamic acid, etc. can be used; and, as the vitamins, pantothenic acid, thiamine, etc. can be used. The feeding culture is preferred as a culturing method.

After the culturing is completed, yeast cells are separated from the culture and washed with water to prepare a yeast suspension. After a density of the yeast cells in the thus prepared yeast suspension is adjusted, the yeast suspension can be used for making dough or bread. The yeast cells can be collected from the thus prepared yeast suspension by means of a rotary vacuum dehydrator, a filter such as a filter press or the like. The thus collected yeast cells are dehydrated to prepare a compressed product of yeast having a water content of from 60 wt % to 75 wt % or the thus dehydrated yeast cells are further dried by means of a dryer to prepare a dry yeast having a water content of from 2 wt % to 10 wt %. Either of the compressed product of yeast or the dry yeast can be used for making dough or bread.

Bread dough according to the present invention is obtained by adding the yeast of the present invention, salt, water and further, if necessary, sugar, skim milk, egg, yeast food, shortening and the like to cereal flour, ordinarily, wheat flour, and by mixing. There are two kinds of typical methods for making dough; that is, a straight dough method and a sponge-dough method. The former is a method in which all the ingredients are mixed at the beginning. The latter is a method in which a sponge is at first made by adding yeast and water to a part of flour and, then, after fermentation, the remaining ingredients are added to the thus made sponge.

As the dough to be added with yeast of the present invention, any dough may be used as long as it is basically made such that a mixture of flour and salt is added with water and mixed. Specifically, illustrated is a dough in which starting materials comprising flour, salt and fat and/or oil are added to auxiliary materials such as sugar, shortening, butter, skim milk, yeast food and egg, etc., if necessary, and, thereafter, to water and, then, mixed.

Next, illustrative methods of making bread are explained.

Bread dough is obtained by adding salt, fat and/or oil, water and the above-obtained yeast cells, preferably, compressed yeast and, further, if necessary, sugar, shortening, butter, skim milk, yeast food, egg and the like to cereal flour, preferably, wheat flour. There are two kinds of typical methods for making bread inclusive of one-loaf bread, buns and the like; that is, a straight dough method and a sponge-dough method. The former is the method in which all ingredients are mixed at a time. The latter is the method in which at first a sponge is made by mixing a part of cereal flour and yeast with water, and then, after fermentation, remaining ingredients are added to the thus made sponge.

In the typical straight dough method, all the ingredients are mixed. The mixture is fermented at a temperature of between 25° C. and 30° C., divided, held intact for a period of bench time, molded and subjected to panning. The resultant dough is subjected to proofing at a temperature of between 35° C. and 42° C. and then baking at a temperature of between 200° C. and 240° C.

In a typical sponge-dough method, about 70% of the whole cereal flour to be used, yeast, yeast food and the like are added to water and, then, mixed. The mixture is fermented at a temperature of between 25° C. and 35° C. for a period of time of between 3 hours and 5 hours, mixed with remaining ingredients such as cereal flour, water, salt and shortening (as dough mixing), divided and held intact for a period of bench time. The resultant dough is molded and then subjected to panning. The dough thus subjected to panning is subjected to proofing at a temperature of between 35° C. and 42° C. and, then, baking at a temperature of between 200° C. and 240° C.

Danish pastries, croissants and the like are made, for example, in the following manner.

To ingredients, such as cereal flour, salt, the above-obtained yeast, sugar, shortening, eggs and skim milk are added water and mixed to prepare dough. Fat and/or oil such as butter and margarine are folded into the thus prepared dough. Rolling and folding are repeated to make multiple layers of the dough and the fat and/or oil. As a method of preparing the dough, illustrated are two methods. In one method, the dough is kneaded such that a temperature of the kneaded dough is as low as about 15° C., and the dough is kneaded without cooling until the intended number of layers is made. In the other method, so-called retarding method, cooling is repeated several times using a refrigerator or a freezer in the course of folding the fat and/or oil.

The obtained dough is rolled, divided, molded and subjected to panning. Thereafter, the dough thus subjected to panning undergoes ordinary steps such as proofing at a temperature of between 30° C. and 39° C. and, then, baking at a temperature of between 190° C. and 210° C.

Illustrative embodiments are described below.

EXAMPLES

Example 1

H-9444 strain, YHK2057 strain, YHK2058 strain, as a reference, Dia Yeast (available from Kyowa Hakko Kogyo Co., Ltd.), commercially available bread yeast 1, commercially available bread yeast 2 and commercially available bread yeast 3 are each subjected to the above-described method to prepare respective compressed product of yeast which are used for tests described below.

1050 g of strong flour, 30 g of each compressed product of yeast, 1.5 g of yeast food (available from Kyowa Hakko Kogyo Co., Ltd. under the trade name of "Pandia C-500") and 630 g of water are mixed (kneaded) by a bread mixer (available from Kanto Kongoki Industrial Co., Ltd. under a type name of "SS type 151") at a low speed for 3 minutes and then at a medium speed for 2 minutes such that a temperature of the thus mixed (kneaded) dough becomes 24° C. The thus obtained dough is fermented at 28° C. for 4 hours. The dough is mixed with 450 g of strong flour, 75 g of sugar, 30 g of salt, 30 g of skim milk and 390 g of water. The resultant mixture is mixed (kneaded) at a low speed for 3 minutes and, then, at a low/medium speed for 2 minutes. The mixed (kneaded) dough is added with 75 g of shortening and mixed (kneaded) at a low speed for 2 minutes, at a low/medium speed for 3 minutes and then at medium/high speed for 3 minutes such that a temperature of the mixed (kneaded) dough becomes 27° C. The thus obtained dough is held intact at a temperature of between 20° C. and 25° C. for 20 minutes and, thereafter, divided into 6 pieces each having 210 g (Pullman). Each piece is molded into ball form. The molded 6 pieces of dough were punched after held intact at a temperature of between 20° C. and 25° C. for 20 minutes. The resultant 6 pieces of dough were put to a 3-pound mold, appropriately molded and fermented at a temperature of 38° C., a humidity of 85% for a period of time of between 50 minutes and 60 minutes to allow the dough to rise to 80% of the inner volume of the mold thereby obtaining a fermented dough. The thus fermented dough in a mold was baked in an oven (available from Sanko Machinery Co., Ltd. under the trade name of NC-GGG-21) at 210° C. for 35 minutes to obtain bread.

8 g of a central portion of each of the thus obtained bread were taken out, added with liquid nitrogen and ground by a mortar into powers. 3 g of the thus obtained powders were introduced into a 22 ml sample bottle (vial), sealed and held at 60° C. for 15 minutes. Thereafter, a concentration of isoamyl alcohol, a concentration of isobutyl alcohol and a concentration of diacetyl were quantitatively analyzed by gas chromatography under the measurement conditions described above. The results are shown in Table 1.

TABLE 1

|  | Isoamyl alcohol (ppm) (A) | Isobutyl alcohol (ppm) (B) | (A)/(B) | Diacetyl (ppm) |
|---|---|---|---|---|
| H-9444 | 20.0 | 11.5 | 1.74 | 2.24 |
| YHK2057 | 32.1 | 17.8 | 1.80 | 1.97 |
| YHK2058 | 10.5 | 6.7 | 1.57 | 1.84 |
| Dia Yeast | 26.5 | 11.2 | 2.37 | 1.40 |
| Commercial bread yeast 1 | 24.7 | 15.2 | 1.63 | 2.72 |
| Commercial bread yeast 2 | 20.2 | 8.2 | 2.46 | 1.04 |
| Commercial bread yeast 3 | 11.3 | 4.9 | 2.31 | 2.21 |

The above-obtained compressed product of yeast was compensated such that the ratio of the yeast in a dry state comes to be 33%. Thereafter, 3 g of the above-described compressed product were added with 20 g of water to prepare a yeast suspension. The obtained yeast suspension and 100 g of strong flour were added with an aqueous solution comprising 30 g of sugar, 0.5 of salt and 32 ml of water and mixed by a complete mixer (available from National Mfg. Co., Ltd., U.S.A.) at 100 rpm for 2 minutes to prepare dough. 20 g of the thus prepared dough were introduced into a 225 ml sample bottle, sealed and held at 30° C. for 5 minutes. An amount of carbon dioxide gas generated at 30° C. for 2 hours in the sample bottle was measured by means of Fermograph II (available from Atto Corporation). The results are shown in Table 2.

TABLE 2

|  | Amount of Carbon dioxide Gas generated (ml/g of dough) |
|---|---|
| H-9444 | 2.50 |
| YHK2057 | 2.40 |
| YHK2058 | 2.35 |
| Dia Yeast | 2.44 |
| Commercial bread yeast 1 | 0.45 |
| Commercial bread yeast 2 | 2.20 |
| Commercial bread yeast 3 | 0.46 |

Each of the bread was evaluated on intensity of fermentation smell and desirability of bread flavor by seven panelists in a sensory way using a five-point method comprising strong (point 5), slightly strong (point 4), medium (point 3), slightly weak (point 2) and weak (point 1).

Evaluation results are shown in terms of that the greater the point in fermentation smell, the less favorable; the greater the point in desirability of bread flavor, the more favorable.

Further, respective specific volumes of the bread were measured using respective comparative bread prepared in the same way as in the above bread except that a part of the preparation step thereof, namely, "divided into 6 pieces each having 210 g (Pullman). Each piece is molded into ball form. The molded 6 pieces of dough were punched after held intact at a temperature of between 20° C. and 25° C. for 20 minutes. The 6 pieces of dough were put to a 3-pound mold, appropriately molded and fermented at a temperature of 38° C. and a humidity of 85% for a period of time of between 50 minutes and 60 minutes to allow the dough to rise to 80% of the inner volume of the mold" was replaced by a newly-set part of the preparation step thereof, namely, "divided to obtain one piece (one loaf) having 450 g. The piece was molded into ball form. The molded piece was punched after held intact at a temperature of between 20° C. and 25° C. for 20 minutes. The piece of dough was put to a mold, molded and fermented at a temperature of 38° C. and a humidity of 85% for a period of time of between 50 minutes and 70 minutes to allow the top of the dough to become 1.5 cm higher than an upper edge of the mold". The results are shown in Table 3.

TABLE 3

|  | Intensity of Fermentation smell | Desirability of Bread flavor | Specific volume (ml/g) |
|---|---|---|---|
| H-9444 | 2.6 | 3.9 | 5.53 |
| YHK2057 | 2.7 | 3.6 | 5.72 |
| YHK2058 | 2.7 | 3.6 | 5.40 |
| Dia Yeast | 3.3 | 3.0 | 5.64 |
| Commercial bread yeast 1 | 3.3 | 3.1 | 5.56 |
| Commercial bread yeast 2 | 3.0 | 3.1 | 5.40 |
| Commercial bread yeast 3 | 3.6 | 2.9 | 5.77 |

A t-test was conducted on H-9444 strain and other strains on the basis of the sensory results.

From the results, it was recognized that, with respect to intensity of fermentation smell and desirability of bread flavor, none of the YHK2057 strain and the YHK2058 strain has a significant difference in a risk rate of 5% from the H-9444 strain whereas all of Dia Yeast, commercial bread yeast 1, commercial bread yeast 2 and commercial bread yeast 3 have a significant difference in a risk rate of 5% from the H-9444 strain.

Example 2

Bread was made by a sponge-dough method according to the composition and method as set forth in Table 4 using H-9444 strain and Dia Yeast (available from Kyowa Hakko Kogyo Co., Ltd.).

TABLE 4

| (Composition) | | |
|---|---|---|
| | | (Parts by weight) |
| Sponge | strong flour | 70 |
|  | yeast | 2 |
|  | yeast food (Pandia C 500) | 0.1 |
|  | water | 42 |
| Dough mixing | strong flour | 30 |
|  | sugar | 5 |
|  | salt | 2 |
|  | shortening | 5 |
|  | skim milk | 2 |
|  | water | 26 |

| (Method) | |
|---|---|
| Mixing | low speed, 3 min.; and low/medium speed, 2 mm. |
| Kneaded dough temperature | 24° C. |
| Fermentation | 28° C., 4 hours |
| Mixing | low speed, 3 min.; low/medium speed, 2 min.; then, after addition of shortening, low speed, 2 min.; low/medium speed, 3 min.; medium/high speed, 3 min. |
| Kneading temperature | 27° C. |

TABLE 4-continued

| Floor time | 20 min. |
|---|---|
| Dividing | (1) 210 g × 6 pieces (Pullman) |
|  | (2) 450 g (one-loaf) |
| Bench time | 20 min. |
| Molding |  |
| Ploofing | 38° C., 85% RH, 50–60 min. |
| Baking | 210–220° C., |
|  | (1) Pullman, 35 min. |
|  | (2) one-loaf, 25 min. |

A sensory test was conducted on the bread (Pullman) and a specific volume was measured on the thus obtained bread (one-loaf) in the same way as in Example 1. The results are shown in Table 5.

TABLE 5

|  | Intensity of Fermentation smell | Desirability of flavor | Specific Bread volume (m/g) |
|---|---|---|---|
| H-9444 | 2.6 | 3.9 | 5.53 |
| Dia Yeast | 3.3 | 3.0 | 5.64 |

As is shown in Table 5, bread which has a weak fermentation smell and has a favorable flavor and taste was obtained by using H-9444 strain.

Example 3

Bread was made by a straight method according to the composition and method as set forth in Table 6 using H-9444 strain and Dia Yeast (available from Kyowa Hakko Kogyo Co., Ltd.).

TABLE 6

| (Composition) | |
|---|---|
| | Parts by weight |
| Strong flour | 100 |
| Yeast | 3 |
| Yeast food (Pandia C-300) | 0.1 |
| Sugar | 5 |
| Salt | 2 |
| Shortening | 5 |
| Skim milk | 2 |
| Water | 68 |

| (Method) | |
|---|---|
| Mixing | low speed, 3 min.; low/medium speed, 2 min.; then, after addition of shortening, low speed, 2 min.; low/medium speed, 3 min.; medium/high speed, 7 min. |
| Kneaded dough temperature | 27° C. |
| Floor time | 28° C., 60 min. |
| Dividing | (1) 210 g × 6 pieces (Pullman) |
|  | (2) 450 g (one-loaf) |
| Bench time | 20 min. |
| Molding |  |
| Ploofing | 38° C., 85% RH, 50–60 min. |
| Baking | 210–220° C., |
|  | (1) Pullman, 35 min. |
|  | (2) one-loaf, 25 min. |

A sensory test was conducted on the thus obtained bread (Pullman) and a specific volume was measured on the bread (one-loaf) in the same way as in Example 1. The results are shown in Table 7.

TABLE 7

|  | Intensity of Fermentation smell | Desirability of flavor | Specific Bread volume (ml/g) |
|---|---|---|---|
| H-9444 | 2.4 | 3.9 | 5.18 |
| Dia Yeast | 3.4 | 2.9 | 5.29 |

As is shown in Table 7, bread which has a weak fermentation smell and has a favorable flavor and taste was obtained by using H-9444 strain.

Example 4

A bun was made by a sugar-added sponge-dough method according to the composition and method as set forth in Table 8 using H-9444 strain and Dia Yeast (available from Kyowa Hakko Kogyo Co., Ltd.).

TABLE 8

(Composition)

|  |  | (Parts by weight) |
|---|---|---|
| Sponge | strong flour | 70 |
|  | glucose | 5 |
|  | yeast | 2 |
|  | yeast food (Pandia C-300) | 0.1 |
|  | whole eggs | 8 |
|  | water | 34 |
| Dough mixing | strong flour | 20 |
|  | weak flour | 10 |
|  | sugar | 20 |
|  | salt | 0.8 |
|  | shortening | 6 |
|  | skim milk | 3 |
|  | water | 18 |

(Method)

| Mixing | low speed, 3 min.; and low/medium speed, 2 mm. |
|---|---|
| Kneaded dough temperature | 25° C. |
| Fermentation | 28° C., 2.5 hours |
| Mixing | low speed, 3 min.; low/medium speed, 2 min.; then, after addition of shortening, low speed, 2 min.; low/medium speed, 3 min.; medium/high speed, 3 min. |
| Kneading temperature | 27° C. |
| Floor time | 28° C., 40 min. |
| Dividing | 50 g |
| Bench time | 20 min. |
| Molding |  |
| Ploofing | 38° C., 85% RH, 60 min. |
| Baking | 200° C, 8–10 min. |

A sensory test was conducted and a specific volume was measured on the bun in the same way as in Example 1. The results are shown in Table 9.

TABLE 9

|  | Intensity of Fermentation smell | Desirability of flavor | Specific Bread volume (ml/g) |
|---|---|---|---|
| H-9444 | 2.3 | 4.1 | 6.16 |
| Dia Yeast | 3.3 | 3.0 | 5.82 |

As is shown in Table 9, the bun which has a weak fermentation smell and has a favorable flavor and taste was obtained by using H-9444 strain.

Example 5

A butter roll was made by a straight method according to the composition and method as set forth in Table 10 using H-9444 strain and Dia Yeast (available from Kyowa Hakko Kogyo Co., Ltd.).

TABLE 10

(Composition)

|  | Parts by weight |
|---|---|
| Strong flour | 80 |
| Weak flour | 20 |
| Yeast | 4 |
| Yeast food (Pandia C-500) | 0.1 |
| Sugar | 15 |
| Salt | 1.5 |
| Shortening | 7 |
| Butter | 8 |
| Skim milk | 2 |
| Whole eggs | 15 |
| Water | 44 |

(Method)

| Mixing | low speed, 3 min.; low/medium speed, 3 min.; then, after addition of shortening, low speed, 2 min.; low/medium speed, 3 min.; medium/high speed, 4 min. |
|---|---|
| Kneaded dough temperature | 27–28° C. |
| Floor time | 28° C., 20 min. |
| Dividing | 50 g |
| Bench time | 20 min. |
| Molding |  |
| Ploofing | 38° C., 85% RH, 60 min. |
| Baking | 200° C., 8–10 min. |

A sensory test was conducted and a specific volume was measured on the butter roll in the same way as in Example 1. The results are shown in Table 11.

TABLE 11

|  | Intensity of Fermentation smell | Desirability of Bread flavor | Specific volume (ml/g) |
|---|---|---|---|
| H-9444 | 2.6 | 3.7 | 5.98 |
| Dia Yeast | 3.4 | 3.0 | 5.90 |

As is shown in Table 11, the butter roll which has a weak fermentation smell and has a favorable flavor and taste was obtained by using H-9444 strain.

As described above in detail, the present invention can provide an yeast capable of making bread excellent in flavor and weak in fermentation smell, a dough containing the yeast, a method for making bread using the yeast and the dough, and a bread made by the method.

What is claimed is:

1. A dough comprising flour and a yeast belonging to the genus Saccharomyces, wherein (A) said yeast produces isoamyl alcohol, isobutyl alcohol and diacetyl in a bread made according to the following steps (1) to (8):

(1) mixing 1050 g of strong flour, 30 g of a compressed product of said yeast, 1.5 g of yeast food and 630 g of water by a bread mixer at 24° C. to prepare dough, (2) fermenting the dough prepared by step (1) at 28° C. for 4 hours to prepare fermented dough, (3) adding 450 g of strong flour, 75 g of sugar, 30 g of salt, 30 g of skim milk and 390 g of water to the fermented dough prepared by step (2) and mixing at 27° C. to prepare dough, (4) allowing the dough prepared by step (3) to stand at a temperature of between 20 and 25° C. for 20 minutes, (5) dividing the dough prepared by step (4) to obtain a 210 g ball of dough, (6) allowing the ball of dough prepared by step (5) to stand at a temperature of between 20 and 25° C. for 20 minutes, (7) punching the ball of dough obtained by step (6), molding the punched dough to a 3-pound bread mold and fermenting the molded dough at 38° C. and 85% humidity such that the dough rises to 80% of the inner volume of the mold, and (8) baking the fermented dough prepared by step (7) in an oven at 210° C. for 35 minutes to make bread; the concentration of isoamyl alcohol being 35 ppm or below, the concentration of diacetyl being 1.5 ppm or above and the ratio of isoamyl alcohol to isobutyl alcohol in concentration being 2 or below, when using gas chromatography to quantitatively determine a head space gas derived from the bread and prepared according to the following steps (a) to (c):

(a) adding liquid nitrogen to 8 g of a central portion of said bread and grinding the central portion into powder using a mortar, (b) introducing 3 g of the powder prepared by step (a) into a 22 ml sample bottle and sealing the bottle, and (c) maintaining the sealed bottle prepared by step (b) at 60° C. for 15 minutes to obtain said head space gas;

and (B) said yeast produces carbon dioxide gas in a dough prepared by mixing 100 g of strong flour, 3 g of compressed product of said yeast and 20 g of water, and 32 ml of water comprising 30 g of sugar and 0.5 g of salt at 100 rpm for 2 minutes, wherein the amount of carbon dioxide gas is 2 ml or above per gram of dough when determined by fermograph according to the following steps (i) to (iii):

(i) introducing 20 g of said dough prepared by (B) into a 225 ml sample bottle and sealing the bottle with a cap connected to a fermograph, (ii) holding the sealed bottle prepared by step (i) at 30° C. for 5 minutes, and (iii) measuring an amount of carbon dioxide gas generated from the sealed bottle at 30° C. for 2 hours by the fermograph.

2. The dough according to claim 1, wherein the yeast belongs to *Saccharomyces cerevisiae*.

3. The dough according to claim 2, wherein the yeast is *Saccharomyces cerevisiae* H-9444 (FERM BP-7153).

4. A process for making bread, comprising the steps of selecting the dough according to any one of claims 1 to 3 and baking said dough.

5. A bread obtained by the process according to claim 4.

* * * * *

UNITED STATES PATENT AND TRADEMARK OFFICE
CERTIFICATE OF CORRECTION

PATENT NO. : 6,649,198 B2
DATED : November 18, 2003
INVENTOR(S) : Toshiaki Imura et al.

It is certified that error appears in the above-identified patent and that said Letters Patent is hereby corrected as shown below:

<u>Title page,</u>
Item [57], ABSTRACT,
Line 1, "an" should read -- a --.

<u>Column 1,</u>
Line 5, "an" should read -- a --.

<u>Column 2,</u>
Line 55, "diaceyl" should read -- diacetyl --.

<u>Column 3,</u>
Line 46, "that" should read -- in which --.

<u>Column 4,</u>
Line 53, "can be separated (screens out)" should read -- a strain having the above-described characteristics can be separated (screened out) from --;
Line 54, "having the above-described" should be deleted; and
Line 55, "characteristics" should be deleted.

<u>Column 6,</u>
Line 8, "kinds of" should be deleted;
Line 29, "kinds of" should be deleted; and
Line 59, "are" should read -- is --.

<u>Column 7,</u>
Line 38, "with" should read -- to --; and
Line 60, "powers." should read -- powders. --.

UNITED STATES PATENT AND TRADEMARK OFFICE
CERTIFICATE OF CORRECTION

PATENT NO. : 6,649,198 B2
DATED : November 18, 2003
INVENTOR(S) : Toshiaki Imura et al.

It is certified that error appears in the above-identified patent and that said Letters Patent is hereby corrected as shown below:

<u>Column 8,</u>
Line 43, "bread" should read -- breads --.

<u>Column 12,</u>
Line 66, "an" should read -- a --.

Signed and Sealed this

Twentieth Day of April, 2004

JON W. DUDAS
*Acting Director of the United States Patent and Trademark Office*